United States Patent [19]

Williamson et al.

[11] Patent Number: 5,250,344
[45] Date of Patent: Oct. 5, 1993

[54] CAST MATERIAL WITH ENCAPSULATED LUBRICANT

[75] Inventors: Tony Williamson, Troutman, N.C.; Martin F. Van Buren, Chelmsford, Mass.; Arthur A. Massucco, Natick, Mass.; Richard S. Lindstrom, Reading, Mass.

[73] Assignee: Zimmer, Inc., Warsaw, Ind.

[21] Appl. No.: 960,183

[22] Filed: Oct. 9, 1992

Related U.S. Application Data

[63] Continuation of Ser. No. 631,587, Dec. 21, 1990, abandoned.

[51] Int. Cl.⁵ .................. B32B 3/00; D06N 7/04; A61F 5/04
[52] U.S. Cl. .................................. 428/143; 428/141; 428/144; 428/147; 428/202; 428/206; 428/402; 428/402.2; 428/402.21; 428/403; 428/407; 428/906; 428/913; 602/2; 602/3; 602/8; 602/9
[58] Field of Search .............. 428/141, 143, 144, 147, 428/156, 159, 160, 224, 402, 402.2, 402.21, 403, 913, 68, 202, 206, 906, 407; 602/5, 6, 9, 11, 20, 21, 2, 3, 8

[56] References Cited

U.S. PATENT DOCUMENTS

| | | | |
|---|---|---|---|
| 3,300,332 | 1/1967 | Gorham et al. | 428/403 |
| 3,415,240 | 12/1968 | Sheldon | 128/90 |
| 4,856,502 | 8/1989 | Ersfeld et al. | 428/913 |

Primary Examiner—Donald J. Loney
Attorney, Agent, or Firm—Todd A. Dawson

[57] ABSTRACT

A slippery orthopedic cast tape produced by depositing onto a substrate a layer of microencapsulated lubricating or friction-reducing material. The substrate is impregnated with a material which is hardenable upon exposure to an activating agent. The coating of each one of the microgranules is formed of a material which is removable upon the application thereto of a removing stimulus. The microencapsulated lubricious material is applied to the inner end of a rolled cast tape so that it will be adjacent the outer layers of a formed cast. In one embodiment, the microgranules are formed of a water-insoluble polymeric coating over a polyethoxylated surfactant which serves as the lubricious material, the polymeric coating being rupturable upon the application of pressure in order to release the lubricious material.

8 Claims, 1 Drawing Sheet

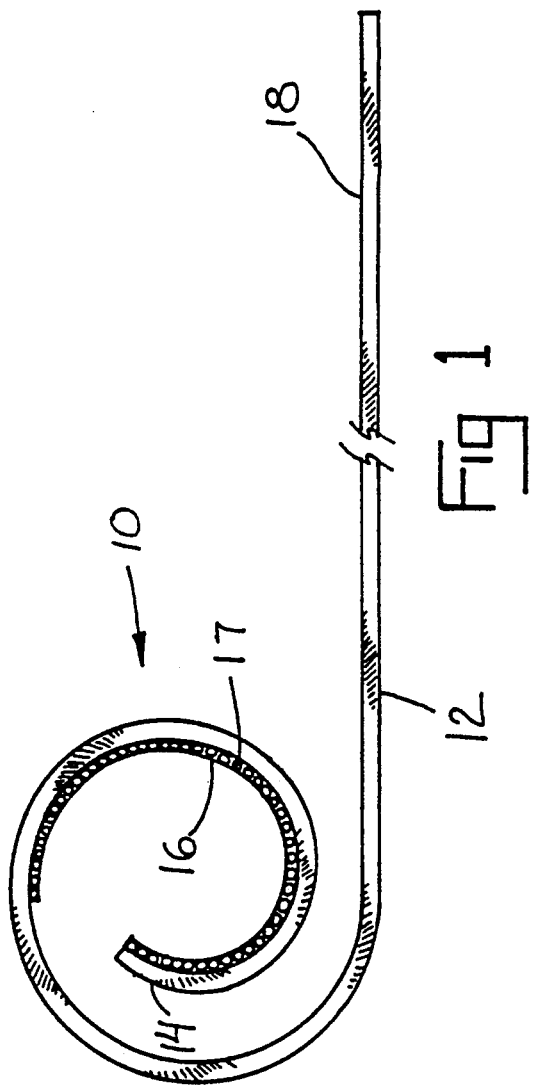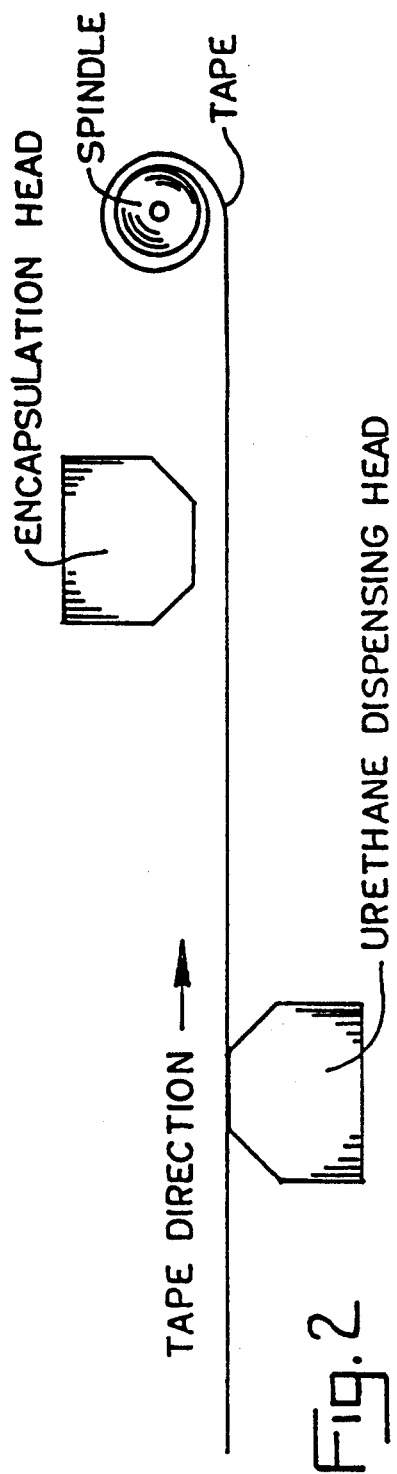

CAST MATERIAL WITH ENCAPSULATED LUBRICANT

This application is a continuation of application Ser. No. 07/631,587 filed Dec. 21, 1990, now abandoned.

BACKGROUND OF THE INVENTION

1. Field of the Invention

The invention relates generally to sheet materials coated with a curable polymeric resin. More particularly, this invention relates to a curable, resin coated sheet material provided with a layer of lubricating material facilitating the use of the sheet material as a synthetic casting tape. Still more particularly, this invention relates to a curable, resin coated sheet material coated with an encapsulated lubricating material which is activated by pressure applied to the material.

2. Description of the Prior Art

Orthopedic cast materials comprising somewhat porous or woven substrates impregnated with a curable resin have been in use for quite some time. The ability of various resins to be pliable when wet and to harden when dry makes them quite suitable for use as an orthopedic cast material. The term resin is generally used herein to mean thermoplastic or water curable polymeric materials (for example, a urethane prepolymer) and the substrates may be formed from a variety of synthetic or natural fabrics such as fiberglass, polyester, cotton, etc. Some resins may be suitable which are activated by activating agents other than water. The substrates and resin may be produced in the form of discrete sheets or elongated strips wrapped into rolls and commonly referred to a synthetic cast tape.

Since any exposure to water will initiate the curing of the polymeric material normally used in synthetic cast tapes, the tapes are packaged in waterproof storage pouches in order to keep the materials dry and pliable prior to use. When the tape is ready for use, it is generally activated by being submerged in water for a short time and then wrapped around the affected limb and allowed to dry and harden into a cast as the resin cures. The resin in the tape hardens rather quickly and, while this feature makes the material quite suitable for use in cast tape, it is also a property which makes the tape tacky and difficult to work with because of the tendency of the resin material in one layer of the tape to stick to the adjacent layer of tape as it is wrapped on the limb. Once the tape is wrapped, some time is required to manipulate the tape to mold it into a cast of proper fit and the progressively increasing tackiness of the resin make it difficult for the technician to slide the various layers around relative to each other to achieve a better fit.

Not only is manipulation of the tape necessary to achieve a proper cast fit, but it is also necessary to insure strength. Because the lamination of cast tape relies on chemical rather than mechanical bonding, the tape must be wrapped firmly to minimize air pockets between the layers. The normal procedure requires the cast tape to be compressed slightly with the palms of the hands to facilitate lamination of the various layers. Since the tape is somewhat tacky at this point, the technician must use a cream or lubricating gel to prevent the tape from lifting up during the finishing process.

The aforementioned problems are solved in part by a prelubricated curable resin coated sheet disclosed in U.S. Pat. No. 4,667,661 (Scholz et al.). The resin coated sheet disclosed in this patent is coated with a lubricant which is present in an amount sufficient to reduce the kinetic coefficient of friction of the sheet material below a certain amount. The lubricant is selected from a variety of materials such as hydrophilic groups which are bonded to the curable resin or an additive, incompatible with the curable resin, such as a surfactant, a polymer comprised of a plurality of hydrophilic groups or a polysiloxane. The prelubricated sheet of the Scholz patent is a sheet which has the lubricant or surfactant coated on its surface prior to wrapping of the sheet about a substrate. While overcoming the aforementioned disadvantages, the Scholz type prelubricated sheet material tends to be slippery immediately after it is removed from the activating water bath. The slipperiness makes it difficult for the technician to hold the tape securely and manipulate it into the form of a well-fitting cast. An additional disadvantage of having the entire tape provided with a lubricious material is that the interlaminar strength of the final cast is compromised due to the interference of the lubricant with the adhesive bond between the layers.

Another prior art cast material which attempts to solve the problem of tackiness during cast formation is shown in U.S. Pat. No. 3,415,243 (Sheldon). This patent shows a cast tape wherein the cast forming reagents are encapsulated in capsules of a rupturable material placed on a substrate. Wrapping the material into a cast and either squeezing or heating the capsules ruptures them and releases the reagents which then intermix to form the hardenable cast material. This tape, however, has no slipperiness and begins to harden quickly after being wet.

It would be advantageous to provide a slippery cast tape material having the advantages of reduced interlaminar friction to facilitate proper cast formation while also having a greater degree of tackiness during the actual wrapping procedure.

It is accordingly an object of this invention to produce a water-curable, resin impregnated sheet material initially able to be firmly grasped during manual manipulation of the sheet material into a laminar cast structure and subsequently able to have some of the various layers of the laminate structure slidably moved relative to each other and relative to a user's hands.

It is another object of this invention to produce a slippery synthetic cast tape which affords the applier thereof greater control than prior art slippery tapes while also providing the requisite degree of slipperiness to facilitate cast formation.

It is a further object of this invention to produce a method and material for easily converting a conventional, non-slippery synthetic cast tape into a slippery synthetic cast tape.

It is yet another object of this invention to produce a method for converting a non-slippery cast tape to a slippery cast tape through the use of an encapsulated lubricious material adapted to be released at or near the end of the cast formation procedure.

It is also an object of this invention to produce a slippery cast tape which maintains the requisite degree of lubrication while not adversely affecting interlaminar adhesive bonds.

SUMMARY OF THE INVENTION

These and other objects are achieved by the preferred embodiment of this invention which comprises an article for use as an orthopedic cast comprising: a planar substrate; a resin material embedded in the substrate, the material being hardenable upon exposure thereof to an activating agent; and a layer of microgranules covering at least a portion of at least one surface of the substrate, each of the microgranules comprising an outer coating covering a core of lubricious material, the outer coating being removable, upon being subjected to a removing stimulus, to release the encapsulated lubricious material.

The invention is also defined by the method of producing a slippery cast tape, the method comprising the steps of encapsulating a lubricious material within a plurality of microgranules the outer coating of which is removable upon the application thereto of a removing stimulus; providing a cast tape containing a cast-forming material which is hardenable upon exposure to an activating agent, depositing the plurality of lubricious-containing microgranules onto only one one end portion of the tape; and rolling the tape so that the portion thereof having the microgranules is on the innermost end of the roll.

BRIEF DESCRIPTION OF THE DRAWINGS

FIG. 1 is a diagrammatic side elevation view of a synthetic cast tape constructed in accordance with the principles of this invention.

FIG. 2 is a diagrammatic view of the method of manufacturing a cast tape in accordance with the principles of this invention.

DESCRIPTION OF THE PREFERRED EMBODIMENT

Referring to FIG. 1, the synthetic cast tape 10 constructed in accordance with the principles of this invention incorporates a substrate 12 of conventional synthetic or non-synthetic materials impregnated with a water curable resin in a conventional manner. Substrate 12 may be a conventional non-slippery cast tape or any other suitable vehicle which may be hardened upon exposure to a certain stimulus. The resin used in the preferred embodiment is a conventional urethane prepolymer although any resin material used in cast tapes would be suitable. The tape is wrapped into a roll, the inner end 14 of which is coated for a predetermined distance with a layer 16 of an encapsulated lubricious material 17. It will be understood that the cast tape may be made in a variety of widths and, when the outer end 18 of the tape is unwrapped from the roll and applied to an affected limb upon which a cast is to be made, the inner end 14 and the encapsulated layer 16 will form the outside layer of the cast being made. Depending upon the length of layer 16 and the size of the limb, one or more layers of the cast will have a lubricious material coating.

While any encapsulation technique may be suitable, in the preferred embodiment the encapsulated layer 16 is formed of a plurality of microcapsules containing within the capsules any suitable lubricious material which, when released by the removal or rupture of the outer coating of the capsules produces a lubricating effect on the layers of the cast tape adjacent thereto. For the purposes of this invention, a variety of solid or liquid lubricious materials may be used within the core of the capsules—for example, lubricants, emulsifiers or surfactants. What is important is that each of these can be used to achieve a slippery cast tape by different mechanisms that are perceived by the user to achieve the same effect—slipperiness. In general, lubrication of adjacent surfaces is provided by oily-type materials that coat both surfaces and produce reduced friction between them. A form of lubrication may also be provided by surface active agents (surfactants) that reduce the interfacial surface tension between the wet layers (i.e. the tape layers as well as between the surgical glove and the cast tape surface). Generally, oil-type lubrication requires larger quantities of material than does surfactant type lubrication. However, for the purposes of this invention both mechanisms will be referred to as lubrication.

The capsules containing the lubricious material are formed so as to be breakable when squeezed by the technician during the formation of the cast. In one preferred embodiment, the capsules, ranging in size from 100 microns to 300 microns, are formed of a water-insoluble polymer known as parylene and contain an ethoxylated surfactant such as Tergitol NP-70. The microencapsulated layer is formed of 97% by volume of Tergitol (available from the Union Carbide Corporation) and 3% by volume of parylene. Parylene is a well-known thermoplastic film polymer based on para-xylylene and made by vapor phase polymerization. A variety of processes are known by which the microencapsulated material of layer 16 may be made and the process of encapsulating the lubricious material forms no part of the invention disclosed herein. Examples of suitable encapsulating methods are disclosed in U.S. Pat. Nos. 3,300,332 (Gorham et al.) and 4,508,760 (Olson et al.)

In a preferred embodiment, the substrate is produced from a knitted fiberglass fabric impregnated with a moisture-cure urethane prepolymer which is normally somewhat sticky. As shown in FIG. 2, the urethane prepolymer is impregnated as the synthetic web moves across a urethane dispensing head. As the impregnated tape continues to move towards a take-up spindle, it passes an encapsulation head from which the microencapsulated material may be dispensed onto the urethane prepolymer. Because the microencapsulated material is granular and dry and because the urethane is somewhat sticky, a layer of the microencapsulated material will stick to the tape as long as it is dispensed from the dispensing head. Obviously, the rate and time at which the microencapsulated material is dispensed and the speed at which the web travels past the dispenser are adjustable to produce a tape 10 with the desired amount of lubricious material 17. The parylene used in the preferred embodiment is preferably used to coat a solid so the ethoxylated surfactant core should preferably be produced in a dry granulated state. While Tergitol NP-70 has been used it has been found that a similar nonylphenol polyethoxylated surfactant known is Iconol NP-70 is available from BASF Corporation which is also suitable for encapsulation by parylene. The Iconol is more easily available commercially in granulated form than the Tergitol.

The invention also encompasses microencapsulation of lubricious material within a capsule which is removable upon exposure to a solvent rather than rupturable upon the application of pressure. For example, the coating could be a water-soluble polymer and the core of the capsule could be any suitable lubricious material compatible with the coating for the particular application described herein.

In addition to the preferred embodiment discussed above, additional examples of encapsulated lubricious materials may be envisioned.

For example, the ability of low concentrations of polyethylene oxide (PEO) and other high molecular weight, water-soluble polymers to reduce hydrodynamic drag is well known. Hence, a variety of water-based PEO solutions are used as industrial lubricants. Moreover, the use of PEO in orthopedic cast tape is taught in U.S. Pat. No. 4,454,873 (Laufenberg et al.). As applied to this invention, PEO granules can be encapsulated within a second polymer having a much slower dissolution rate in water. These encapsulated granules can then form the encapsulated layer 16 applied to the cast tape during manufacture. When the tape is activated in water, the outer coating will become substantially weakened so that the mechanical action of rubbing by the technician will cause release and dissolution of the PEO resulting in lubrication between the technician's gloves and the surface of the wet cast tape. It is anticipated that polyvinyl alcohol and its copolymers would be excellent candidates for the outer (encapsulation) coating on the PEO particles. Other examples of encapsulating/lubricating polymer pairs can be selected from the family of water-swellable/water-soluble polymers such as the polyacrylamides, polyvinylpyrrolidone, the modified celluloses, cellulose acetate, and hydroxyhilic acrylics.

It is also envisioned that liquid lubricants and mixtures of liquid lubricants, or of liquid and solid, or other mixture combinations may be used for the core of the microcapsules are applicable. For example mixtures of Gantrez AN-119 (a vinylmethyl ether copolymer) and AVICEL RC 591F (microcrystalline cellulose) have been found to impart good lubricating properties to the surfaces of wet cast tapes. Both are solids and can be encapsulated with a water-soluble or water-swellable polymer. Mixtures of Tween 20 and 80 surfactants (liquid ethoxylated sorbates) have also been found effective as have mixtures of the Tween surfactants with Silwet L-7001 (an ethoxylated silicone). These materials or mixtures of these materials can be encapsulated using methods such as spray drying and coacervation to provide control over the release of the lubricant.

Another embodiment of the invention involves the use of coated rather than microencapsulated films. For example, coated PEO film can be slit or cut into various geometrical shapes and applied to the surface of the cast tap during manufacture. Again, a variety of water-soluble/water-swellable polymers can be used to control the dissolution rate of the PEO. If the film is slit into small enough pieces, say ⅛" on a side, water-insoluble polymers should also be effective as coating materials since dissolution of the PEO would commence at the exposed edges of the film composite, and the PEO dissolution rate could be controlled and then rapidly accelerated by mechanical action which would serve to remove the water-insoluble film coating. This embodiment could be modified to include coated chopped fibers of PEO.

It is also envisioned that the controlled release of PEO from PEO films could be achieved by forming surface coatings through reaction, for example, with reactive surface coatings of various urethanes and acrylics.

It is intended that this invention emcompass various types of cast tape structures which ca be adapted to produce controlled release of the lubricious material so that the cast tape can be applied without any substantial lubricant—that is, with some tackiness—until the wrapping procedure is essentially completed. This allows improved control over the tape wrapping procedure. The major portion of the lubricious material would then become available, when needed, during the reduction of the fracture and/or the shaping of the cast tape just prior to setting.

It will be understood by those skilled in the art that numerous other modifications and improvements may be made to the preferred embodiment of the invention disclosed herein without departing from the spirit and scope thereof.

What is claimed is:

1. An article for use as an orthopedic cast comprising:
    a planar substrate having an end;
    a resin material embedded in said substrate, said material being hardenable upon exposure thereof to an activating agent; and
    a layer of microgranules covering only a portion of at least one surface of said substrate adjacent said end, each of said microgranules comprising an outer coating covering a core of lubricious material, said outer coating being removable upon being subjected to a removing stimulus to release said core of lubricious material.

2. An article according to claim 1 wherein said outer coating is rupturable upon application of pressure thereto.

3. An article according to claim 1 wherein said outer coating is dissolvable by a solvent.

4. An article according to claim 1 wherein said lubricious material is a surfactant.

5. An article according to claim 1 wherein said lubricious material is polyethylene oxide.

6. An article according to claim 1 wherein said planar substrate is in the form of a tape and said microgranular layer covers only a predetermined length of one end of said tape.

7. An article according to claim 6 wherein said tape is, prior to use, rolled and wherein said microgranular layer covers the innermost end of said tape whereby, when said tape is wrapped to form a cast, said microgranular layer will only be situated in a predetermined number of layers of said tape proximate a surface of said cast.

8. An article for use as an orthopedic cast comprising:
    a planar substrate having an end;
    a hardenable material impregnated in said substrate, said material being hardenable upon exposure to an activating agent;
    a layer of microgranules covering only a portion of at least one surface of said impregnated substrate adjacent said end, each of said microgranules comprising a core and a coating, said core comprising a first water-soluble polymer for reducing friction between adjacent layers of said substrate as the latter is shaped into a cast, said coating comprising a second water-soluble polymer, a dissolution rate of said second water-soluble polymer being slower than that of said first water-soluble polymer.

* * * * *